United States Patent [19]

Morin, Jr.

[11] Patent Number: 4,665,066

[45] Date of Patent: May 12, 1987

[54] 3-THIAZOLOMETHYL CEPHALOSPORINS AS ANTIBIOTICS

[75] Inventor: John M. Morin, Jr., Indianapolis, Ind.

[73] Assignee: Eli Lilly and Company, Indianapolis, Ind.

[21] Appl. No.: 685,676

[22] Filed: Dec. 24, 1984

[51] Int. Cl.$^4$ .................. A61K 31/545; C07D 501/46
[52] U.S. Cl. ................................ 514/206; 548/159; 540/227
[58] Field of Search ...................... 544/27, 21; 514/206

[56] References Cited

U.S. PATENT DOCUMENTS

| | | | |
|---|---|---|---|
| 4,165,430 | 8/1979 | Bradshaw et al. | 540/222 |
| 4,168,309 | 9/1979 | Ayres et al. | 540/224 |
| 4,275,062 | 6/1981 | Brewer et al. | 540/221 |
| 4,425,340 | 1/1984 | Teraji et al. | 514/206 |
| 4,476,123 | 10/1984 | Labeeuw et al. | 514/206 |
| 4,500,526 | 2/1985 | Imae et al. | 540/227 |
| 4,507,487 | 3/1985 | Kamachi et al. | 548/194 |

FOREIGN PATENT DOCUMENTS

| | | | |
|---|---|---|---|
| 0137441 | 4/1985 | European Pat. Off. | |
| 0164122 | 12/1985 | European Pat. Off. | 540/227 |
| 60-67483 | 4/1985 | Japan | 540/227 |
| 166689 | 8/1985 | Japan | 540/227 |

OTHER PUBLICATIONS

Fujimoto et al., "Cephalosporin Antibiotics . . . ", Chem. Abst. 103: 178066j, (1984).
McOmie, J. F. W., *Protective Groups in Organic Chemistry*, Plenum Press (1973), New York, pp. 192, 193, 204.
Fujimoto, K., et al., "Annual Report of Sankyo Research Laboratories", vol. 36, Dec. 1984, pp. 93–113.
Derwent Abstract 85-130958/22.

*Primary Examiner*—Donald G. Daus
*Assistant Examiner*—G. Hendricks
*Attorney, Agent, or Firm*—William B. Scanlon; Leroy Whitaker

[57] ABSTRACT

7$\beta$-[2-(2-Aminothiazol(oxazol)-4-yl)-2-oximinoacetamido]-3-(thiazolium or substituted thiazolium-3-yl)methyl-3-cephem-4-carboxylates and the correspondingly substituted 1-oxadethia and 1-carbadethia 3-cephem compounds are potent antibacterials useful in a therapeutic method for treating bacterial diseases. Also provided are pharmaceutical formulations of these thiazolium-substituted compounds and intermediates useful in the preparation thereof.

6 Claims, No Drawings

3-THIAZOLOMETHYL CEPHALOSPORINS AS ANTIBIOTICS

BACKGROUND OF THE INVENTION

This invention relates to semi-synthetic β-lactam antibiotic compounds, compositions thereof, a method for combating infectious bacteria, and to intermediates useful in the preparation of the antibiotic compounds. In particular, it relates to β-lactam compounds substituted by a thiazolium or substituted thiazolium group.

Numerous cephalosporin antibiotics having a quaternary amino or betaine structure at the 3'-position of the 3-cephem ring system have been described since Abraham et al. described cephalosporin $C_a$ (pyridine), Hale, Newton, and Abraham, *Biochem. J.*, 79, 403 (1961). One such quaternary ammonium substituted cephalosporin known as cephaloridine, 7-(2-thienylacetylamino)-3-(pyridinium-1-ylmethyl)-3-cephem-4-carboxylate, has achieved clinical importance as an antibotic. Other recent quaternary ammonium substituted cephalosporins of commerical interest include that described by Ochiai et al., 7-[2-(2-aminothiazol-4-yl)-2-methoxyiminoacetamido]-3-(pyridinium-1-ylmethyl)-3-cephem-4-carboxylate, in U.S. Pat. No. 4,278,671 and ceftazidime, 7-[2-(2-aminothiazol-4-yl)-2-(2-carboxyprop-2-yl)oxyiminoacetamido]-3-(pyridinium-1-ylmethyl)-3-cephem-4-carboxylate, in U.S. Pat. No. 4,258,041.

Because of the interesting antibacterial properties of cephalosporin substituted with a quaternary ammonium group, extensive research continues to discover new β-lactam antibiotics with greater potency against various microorganisms.

SUMMARY

The compounds provided by this invention are represented by the following structural formula 1.

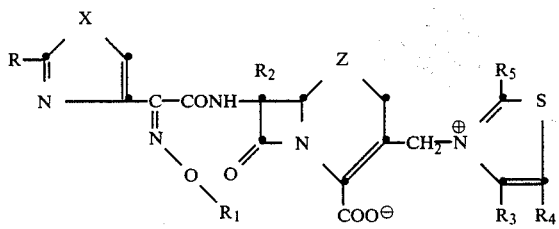

wherein R is for example amino, X is an oxygen atom or a sulfur atom, $R_1$ represents hydrogen, an alkyl group, or a substituted alkyl group, $R_2$ is hydrogen, an alkoxy group, or an alkylthio group, Z is a sulfur atom, an oxygen atom, or a carbon atom, which may be substituted, and $R_3$, $R_4$, and $R_5$ are independently hydrogen or a substituent group.

The compounds of the above formula 1 are prepared by the nucelophilic displacement with the appropriate thiazole of a 3-halomethyl or a 3-acyloxymethyl cephalosporin starting material having in the 7-position the acyl side chain corresponding to the formula 1 compound. Alternatively, the compounds can be prepared by the N-acylation of a 7-amino-3-thiazoliummethyl-3-cephem nucleus compound with the desired acyl moiety.

The compounds of the invention inhibit the growth of microorganisms pathogenic to man and animals and can be used in the treatment of bacterial infections.

DETAILED DESCRIPTION

The thiazolium substituted cephalosporins of this invention are represented by the above formula 1 wherein X is O or S; Z is O,

or $=C(R_6)(R_7)$, wherein m is 0 or the integer 1, $R_6$ and $R_7$ are independently hydrogen or $C_1$–$C_3$ alkyl;

R is hydrogen, hydroxy, amino and its tautomeric imino form, or protected amino;

$R_1$ is hydrogen, $C_1$–$C_4$ alkyl, or $C_1$–$C_4$ alkyl substituted by carboxy, protected carboxy, $C_1$–$C_4$ alkoxycarbonyl, a carboxamido group represented by the formula —$CON(R_8)(R_9)$ wherein $R_8$ and $R_9$ are independently hydrogen, or $C_1$–$C_3$ alkyl; or $R_1$ is a group represented by the formula

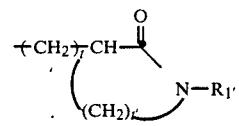

wherein t=0–3, t'=2–4, and $R_1'$ is H or $C_1$–$C_4$ alkyl;

$R_2$ is hydrogen, $C_1$–$C_4$ alkoxy, $C_1$–$C_4$ alkylthio, amino, or —NHCHO;

$R_3$, $R_4$, and $R_5$ are independently hydrogen, $C_1$–$C_4$ alkyl, $C_1$–$C_4$ alkoxy, hydroxy, cyano, carboxy, $C_1$–$C_4$ alkoxycarbonyl, amino, $C_1$–$C_4$ alkanoylamino, halogen, $C_1$–$C_4$ alkanoyloxy, and $C_1$–$C_4$ alkylsulfonyloxy; or $C_1$–$C_4$ alkyl substituted by hydroxy, $C_1$–$C_4$ alkanoyloxy, $C_1$–$C_4$ alkylsulfonyloxy, $C_1$–$C_4$ alkoxy, halogen, cyano, carboxy, or $C_1$–$C_4$ alkoxycarbonyl, hydroxyimino, or $C_1$–$C_3$ alkoxyimino; and $R_3$ and $R_4$ can be taken together with the ring to which they are attached to form a $C_5$ to $C_8$ carboxyclic ring; and the pharmaceutically acceptable non-toxic salts thereof.

In the above formula 1, the term $C_1$–$C_4$ alkyl refers to the straight and branched chain alkyl groups having from 1 to 4 carbon atoms such as methyl, ethyl, n-propyl, isopropyl, n-butyl, isobutyl, and the like; $C_1$–$C_4$ alkyl substituted by carboxy refers to the straight and branched chain alkyl groups substituted by a carboxy such as carboxymethyl, 2-carboxyethyl, 1-carboxyethyl, 3-carboxypropyl, 2-carboxypropyl, 4-carboxybutyl, 2-carboxyprop-2-yl, and like carboxy substituted alkyl groups; $C_1$–$C_4$ alkyl substituted by protected carboxy refers to such groups as those mentioned above wherein the carboxy group of the carboxy alkyl is protected by a conventional carboxy group among which may be mentioned such groups as allyl, t-butyl, benzyl, diphenylmethyl, 4-methoxybenzyl, 4-nitrobenzyl, a haloalkyl group such as 2,2,2-trichloroethyl, 2-iodoethyl, silyl ester for example a trialkylsilyl ester group such as trimethylsilyl, triethylsilyl, dimethyl t-butyl-silyl, and like carboxy protecting groups. Likewise, the carboxy group of the carboxy substituted alkyl group such as those mentioned above may be in the form of an ester of a $C_1$–$C_4$ alcohol to form a $C_1$–$C_4$ alkoxycarbonyl substituted alkyl group, for example the methyl ester, the ethyl ester, the t-butyl ester, and the like. The term $C_1$–$C_4$ alkyl substituted by a carboxamido group represented by the formula —$CON(R_8)(R_9)$ refers to the amide form of the carboxy substituted alkyl group, for example those mentioned above, and includes the primary, secondary and tertiary amides such as aminocarbonylmethyl, 2-aminocarbonylethyl, 1-aminocarbonylethy, 2-aminocarbonylprop-2-yl, 3-aminocarbonylbutyl, methylaminocarbonylmethyl, 1-dimethylaminocarbonylethyl, 2-(n-propyl)aminocarbonylethyl, 3-diethylaminocarbonylpropyl, and like carboxamido substituted alkyl groups.

Examples of $C_1$–$C_4$ alkoxy groups represented by $R_2$ are the straight and branched chain alkyl ether groups such as methoxy, ethoxy, isopropoxy, n-propoxy, n-butoxy, and the like; while examples for the $C_1$–$C_4$ alkylthio group represented by $R_2$ include such groups as the straight and branched alkyl chain thioether groups such as methylthio, ethylthio, n-propylthio, n-butylthio, n-isopropylthio, and the like.

With respect to the thiazolium substituent in the 3'-position, the terms $R_3$, $R_4$, and $R_5$ may be hydrogen or a substituent group as defined hereinabove. Examples of such substitutent groups include the $C_1$–$C_4$ alkyl groups and the $C_1$–$C_4$ alkoxy groups such as those exemplified hereinabove for the terms $R_1$ and $R_2$. Examples of $C_1$–$C_4$ alkanoylamino groups are acetylamino, propionylamino, butyrylamino, iso-butyrylamino, formylamino, and the like. Examples of $C_1$–$C_4$ alkyl substituted groups include those substituted by hydroxy, for example hydroxymethyl, 2-hydroxyethyl, 1-hydroxyethyl, 3-hydroxypropyl, 4-hydroxybutyl, 3-hydroxybutyl, and the like; $C_1$–$C_4$ alkyl substituted for $C_1$–$C_4$ alkanoyloxy includes for example 2-acetoxyethyl, 1-acetoxyethyl, 2-formyloxyethyl, 3-acetoxypropyl, 2-propionoxyethyl, 2-butyryloxyethyl, 4-acetoxybutyl, and the like; $C_1$–$C_4$ alkyl substituted by $C_1$–$C_4$ alkylsulfonyloxy is exemplified by such groups as 2-methylsulfonyloxyethyl, 3-methylsulfonyloxypropyl, 3-ethylsulfonyloxypropyl, 2-methylsulfonyloxypropyl, 2-propylsulfonyloxyethyl, 4-methylsulfonyloxybutyl, and the like; $C_1$–$C_4$ alkyl substituted by $C_1$–$C_4$ alkoxy is exemplified by such groups as methoxymethyl, 2-methoxyethyl, 1-ethoxyethyl, 2-ethoxyethyl, 3-methoxypropyl, 2-methoxybutyl, 2-(t-butoxy)ethyl, and the like; $C_1$–$C_4$ alkyl substituted by halogen is exemplified by such groups as 2-chloroethyl, 2-bromoethyl, 3-chloroethyl, 4-chlorobutyl, trifluoromethyl, 2-fluoroethyl, 4-bromobutyl, 3-chlorobutyl, and the like; $C_1$–$C_4$ alkyl substituted by cyano is exemplied by 2-cyanoethyl, 3-cyanopropyl, 2-cyanobutyl, cyanomethyl, and the like; while $C_1$–$C_4$ alkyl substituted by carboxy is represented by such groups as carboxymethyl, 2-carboxyethyl, 3-carboxypropyl, 4-carboxybutyl, 2-carboxypropyl, 2-carboxybutyl, 3-carboxybutyl, and the $C_1$–$C_4$ alkyl esters of such carboxy-substituted alkyl groups, and the like; $C_1$–$C_4$ hydroxyimino refers to hydroxyiminomethyl, 1-hydroxyiminoethyl, 2-hydroxyiminoethyl, 3-hydroxyiminopropyl, and 4-hydroxyiminobutyl, while $C_1$–$C_4$ substituted by $C_1$–$C_3$ alkoxyimino refers to methoxyiminomethyl, ethoxyiminomethyl, 1-methoxyiminoethyl, and the like.

The compounds represented by the formula 1 can be prepared via two general routes. First, a compound represented by the following formula 2 is allowed to react with thiazole or a substituted thiazole represented by the formula 3.

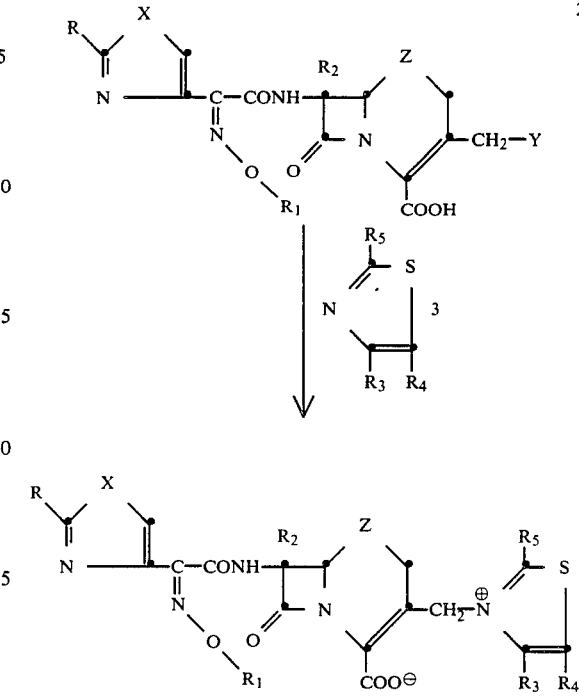

In the above formulae 3 and 4, R, $R_1$, $R_2$, $R_3$, $R_4$, $R_5$, X, and Z have the same meanings as defined above for formula 1 and Y is an acyloxy group such as a $C_1$–$C_4$ alkanoyloxy group, for example acetoxy, or a halo group such as chloro, bromo, or iodo. The reaction is carried out in an inert solvent at a temperature between about 20° C. and about 65° C. An excess of the thiazole or substituted thiazole is used for best results. When in the formula 2, Y is a halo group, the reaction proceeds at about room temperature and can be carried out at higher temperatures of up to about 65° C. When Y is an acyloxy group such as acetoxy, the reaction is usually carried out with warming at temperatures of about 45° C. to about 65° C. A small amount of an iodide salt, e.g. KI, when added to the reaction mixture (Y=acyloxy), oftentimes enhances the rate and yield of the displacement reaction. The compound of the formula 2 wherein R is amino and $R_1$ is a carboxy-substituted alkyl group may be used in the reaction in protected form, i.e. where the amino and carboxy groups are suitably protected with conventional amino and carboxy-protecting groups.

The starting materials (formula 2) are obtained by the N-acylation of a 7-amino-3'-substituted-3-cephem nucleus compound with the desired oximino-substituted acetic acid derivative as shown below.

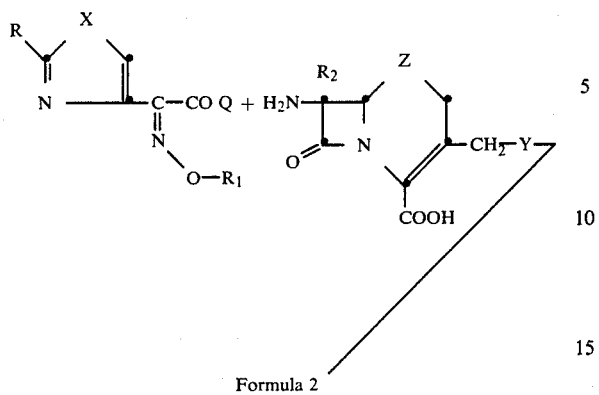

Formula 2

The N-acylation is carried out by conventional methods, e.g. Q can be an active derivative of the carboxy group such as a halogen atom, azido, an active ester, or the like. Any carboxy and amino groups present in the oximino acetic acid may be protected, while the carboxy group of the 7-amino nucleus compound also is protected for best results.

The compounds represented by the formula 1 are also obtained by a second route which comprises the N-acylation of a 7-amino-3'-thiazolium-3-cephem nucleus compound represented by the following formula 4.

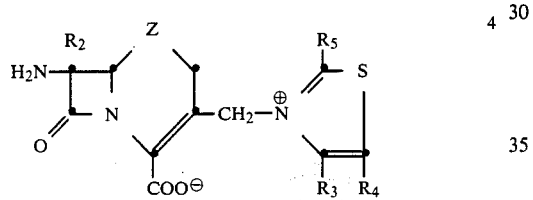

wherein Z, $R_2$, $R_3$, $R_4$, and $R_5$ have the same meanings as defined for formula 1. The acylation is carried out with an oximino-substituted acetic acid represented by the formula,

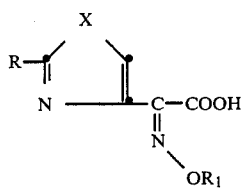

wherein X, R, and $R_1$ have the same meanings as defined for formula 1, or with a carboxy activated derivative thereof. For purposes of the acylation, when R is amino, and $R_1$ is hydrogen or a carboxy-substituted alkyl group, the amino, hydroxy or carboxy groups are suitably protected with a conventional protecting group.

Active derivatives of the carboxy group of the oximino-substituted acetic acid are, for example, the acid halides, acid azides, active esters, or acid anhydrides. Active esters formed with methyl chloroformate, isobutyl chloroformate, N-hydroxysuccinimide, N-hydroxybenztriazole, and acid anhydrides formed with acetic acid, chloroacetic acid, propionic acid, and like derivatives are useful.

The compounds of the invention (formula 1) wherein $R_1$ is $C_1$-$C_4$ alkyl or $C_1$-$C_4$ alkyl substituted by carboxy are obtained by the alkylation of a hydroxyiminoacetic acid ester as shown in the following reaction scheme.

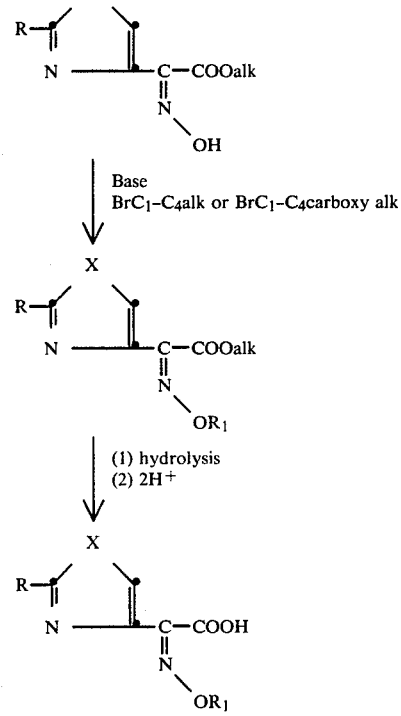

alk = $C_1$-$C_4$ alkyl.

The alk ester, e.g. the ethyl ester of the hydroxyimino acid is alkylated with a $C_1$-$C_4$ alkyl halide, preferably a bromide or iodide in the presence of a strong base such as sodium hydride or strong alkali in an inert solvent. Examples of alkyl halides which may be used are methyl bromide, ethyl iodide, isopropyl bromide, and the like.

The alkylation with a carboxy-substituted $C_1$-$C_4$ alkyl halide is carried out similarly; however, the carboxy group is desirably protected with a carboxy-protecting ester group during the alkylation. Suitable protecting ester groups are e.g. t-butyl, p-methoxybenzyl, and p-nitrobenzyl. Examples of carboxy-substituted alkyl halides which can be used are t-butyl bromoacetate, t-butyl bromopropionate, t-butyl 2-bromoprop-2-ylcarboxylate, and the like. The carboxy-substituted $C_1$-$C_4$ alkyl halide may be in the amide form to obtain the corresponding amide in the alkylation.

Alkylation of the hydroxyimino group ($R_1$=H) with a haloalkyl group of the formula

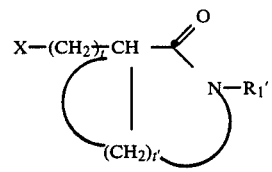

wherein X is chloro, bromo, or iodo, and $R_1'$, t, and t' are as defined above also is accomplished in the same manner.

The 7-amino-3'-thiazolium-substituted-3-cephem nucleus compound (formula 4) is obtained by the N-deacylation of a 7acylamido-3'-thiazolium-substituted-3-cephem-4-carboxylate. The N-decylation is carried out in an inert solvent by reaction with an imino halide-forming reagent such as phosphorus pentachloride to provide the intermediate imino halide derivative of the 7-amido group. The imino halide intermediate is reacted with an alcohol such as methanol or isobutanol to form the corresponding imino ether. The latter on decomposition affords the 7-amino nucleus compound (formula 4).

A preferred route to the compounds represented by the formula 1 comprises the use of a compound of the formula 2 wherein Y is iodo and the carboxy group in the 4-position and any amino group substituents are protected by silylation such as with a trialkylsilyl group. In preparing a compound of the invention, a formula 2 compound wherein Y is an acyloxy group, e.g. acetoxy, is first silylated to block the reactive carboxy group and any amino groups present in the molecule. The silylation can be accomplished with the commonly employed silylating agents, for example mono -or bis-trimethylsilylacetamide or, preferably, with N-methyl-N-trimethylsilyltrifluoroactamide. The silylation is carried out in an inert solvent, preferably aprotic, such as a halogenated solvent, e.g. methylene chloride, chloroform, chloroethane, or trichloroethane or other inert solvent such as acetonitrile. The silylated derivative is then reacted with trimethylsilyliodide (TMSI) to form the corresponding silylated 3-iodomethyl derivative. The solution of the latter derivative is evaporated to dryness and the residual derivative is dissolved in an insert solvent such as acetonitrile and treated in solution with a slight excess of tetrahydrofuran to degrade excess TMSI. To this solution is then added thiazole or a substituted thiazole represented by the formula 3 to form a silylated compound of the invention (formula 1) by displacement of the iodo group. The silyl blocking groups are hydrolyzed to form a compound of formula 1.

The above-described preparation is illustrated in the following reaction scheme.

Formula 2

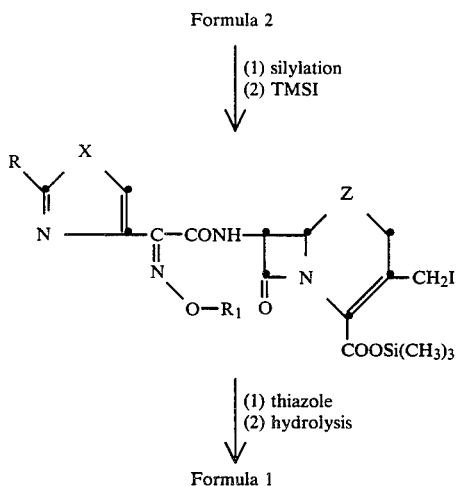

Formula 1

The silylating reagent is preferably a trialkylsilyl group donor such as trimethylsilyl, triethylsilyl, dimethylethylsilyl, dimethyl-t-butylsilyl and the like. The above-described formation of the 3-iodomethyl silylated derivatives is essentially the method of Bonjouklian, U.S. Pat. No. 4,266,049.

Alternatively, the compound of the invention may be obtained with a 7-formamido nucleus compound represented by the formula,

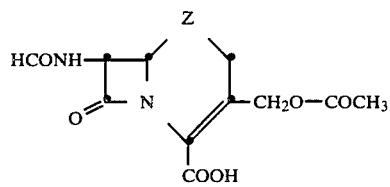

wherein Z has the same meanings as defined for formula 1. According to this preparative method, the 7-formamido compound is silylated as described hereinabove and is reacted with TMSI to provide the silylated 3-iodomethyl compound. The latter is reacted with thiazole or a substituted thiazole and hydrolyzed in methanolic hydrochloric acid to effect removal of the N-formyl group to provide the 7-amino nucleus compound represented by formula 4. The latter is then N-acylated with the appropriate oxazole or thiazole oximinoacetic acid derivative to provide the compound of formula 1.

In carrying out the above-described preparation of formula 1 compounds via the TMSI route, the 3-iodomethyl silylated derivative can be reacted with a silylated substituted thiazole. For example, a carboxymethyl substituted thiazole may be silylated in solution and the solution added to the solution of the 3-iodomethyl derivative.

Examples of thiazoles which can be used to prepare the compounds of the formula 1 are thiazole, 4-methylthiazole, 4-ethylthiazole, 4-methyl-5-ethylthiazole, 5-ethylthiazole, 4,5-dimethylthiazole, 2-methyl-thiazole, 2-methoxythiazole, 4-ethoxythiazole, 5-hydroxythiazole, 4-methyl-5-(2-acetoxyethyl)thiazole, 4-methyl-5-(2-formuloxyethyl)thiazole, 4-methyl-5-methoxycarbonylthiazole, 5-carboxythiazole, 4-methyl-5-carboxymethylthiazole, 4,5-dihydroxythiazole, 2-hydroxythiazole, 2-aminothiazole, 4-aminothiazole, 2-acetylaminothiazole, 2-acetylamino-4-methylthiazole, 2-methyl-4-(2-chloroethyl)thiazole, 4-methyl-5-chloromethylthiazole, 2-(2-hydroxyethyl)thiazole, 4-methyl-5-(2-hydroxyethyl)thiazole, 4-amino-2-(2-hydroxyethyl)thiaziole, 4-methyl-2-(3-hydroxypropyl)-thiazole, 4-methyl-(2-hydroxypropyl)thiazole, 2-methyl-4-hydroxymethylthiazole, 2-ethoxythiazole, 4-methoxythiazole, 4,5-dimethoxythiazole, 4-amino-5-ethoxythiazole, 4-methylsulfonyloxythiazole, 2-ethyl-4-methoxymethylthiazole, 2-acetylamino-4-(2-ethoxyethyl)thiazole, 2-methyl-4-carboxymethylthiazole, 4-ethyl-5-(2-carboxyethyl)thiazole, 2-(2-methylsulfonyloxyethyl)thiazole, tetrahydrobenzthiazole(4,5-cyclohexanothiazole), 4,5-cyclopentanothiazole, 4,5-cycloheptanothiazole, 4,5-cyclooctanothiazole, and like thiazoles.

The 7-position amino group of the nucleus 4 is acylated as described hereinabove with the appropriate oximino-substituted acetic acid in the form of an active carboxylic acid derivative. Examples of oximino-substituted acetic acids used in the preparation of formula 1 compunds are 2-(2-aminothiazol-4-yl)-2-hydroxyiminoacetic acid, 2-(2-aminothiazol-4-yl)-2-methoxyiminoacetic acid, 2-(2-aminooxazol-4-yl)-2-methoxyiminoacetic acid, 2-(2-aminothiazol-4-yl)-2-carboxymethoxyiminoacetic acid, 2-(2-aminothiazol-4-yl)-2-ethoxycarbonylmethoxyiminoacetic acid, 2-(2- aminooxazol-4-yl)-2-aminocarbonylmethoxyiminoacetic acid, 2-(2-aminothiazol-4-yl)-2-(2-carboxyprop-2-yl)-oxyiminoacetic acid 2-(2-aminothiazol-4-yl)-2-(2-pyrrolidone-3-yl)oxyiminoacetic acid, 2-(2-aminothiazol-4-yl)-2-(N-methylaminocarbonyl)methoxyiminoacetic acid, 2-(2-aminooxazol-4-yl)-2-hydroxyiminoacetic acid, 2-2-aminothiazol-4-yl)-2-ethoxyiminoacetic acid, 2-thiazol-4-yl)-2-methoxyiminoacetic acid, 2-(oxazol-4-yl)-2-methoxyiminoacetic acid, 2-(2-hydroxyoxazol-4-yl)-2-methoxyiminoacetic acid.

During the N-acylation of 4 with an amino-substituted acetic acid wherein R is an amino group, the amino group of the 2-aminothiazole or 2-aminooxazole ring is preferably protected to prevent undesired N-acylation. Commonly used amino-protecting groups may be used, for example trityl, formyl, acetyl, haloacetyl, alkoxycarbonyl, and arylalkoxycarbonyl such as t-butyloxycarbonyl, ethoxycarbonyl, allyloxycarbonyl, t-amyloxycarbonyl, adamantyloxycarbonyl, benzyloxycarbonyl, p-nitrobenzyloxycarbonyl, and like conventional amino-protecting groups. Likewise, when $R_1$ is a carboxy-substituted alkyl group, the carboxy group is desirably protected during acylation of 4. Typical conventional carboxy-protecting groups which can be used for this purpose are allyl, t-butyl, trichloroethyl, benzyl, 4-nitrobenzyl, 4-methoxybenzyl, diphenylmethyl, and trialkylsilyl, e.g. trimethylsilyl.

The compounds of the invention wherein Z is an oxygen atom or a carbon atom $[C(R_6R_7)]$ are obtained according to the preparative methods and with the intermediates described by U.S. Pat. Nos. 4,226,866, 4,366,316, and the N-acylation and nucleophilic substitution reactions described hereinabove. The compounds represented by formula 1 wherein Z is

are obtained by the N-acylation of 7-aminocephalosporanic acid (7-ACA, m=0), or the 1-oxide thereof (m=1), followed by nucleophilic substitution of the 3'-acetoxy group with thiazole or a substituted thiazole. Alternatively, 7-ACA or the 1-oxide thereof is reacted with the thiazole or substituted thiazole and the 7-amino thiazolium nucleus compound N-acylated with the oximino-substituted acetic acid as described hereinabove.

The compounds of the invention wherein Z is

and m is 1, cephalosporin 1-oxides, are useful inter alia for preventing the formation of the 2-cephem isomers of the formula 1 compounds. During the nucleophilic displacement reaction with a thiazole or substituted thiazole, the double bond of the 3-cephem starting material (m=0) can migrate to the 2-position to some extent. Such 2-cephems have lowered antibacterial activity and, when isomerization occurs to an appreciable extent, are desirably separated from the 3-cephem isomer, e.g. via chromatography. The use of the starting material in the 1-oxide form (m=1) prevents such isomerization. The 1-oxide form of the compounds 1 wherein (m=0) also exhibit antibacterial activity and enzyme inhibitory activity in their own right and may be used for such purposes.

The compounds of the invention wherein R is an amino group can exist in the tautomeric form as shown below.

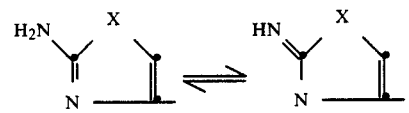

which form is encompassed in this invention.

Examples of compounds of the invention represented by the formula 1 are listed in the following Table 1 wherein reference is made to formula 1.

TABLE 1

| X | Z | R | $R_1$ | $R_2$ | Thiazole |
|---|---|---|---|---|---|
| O | S | $NH_2$ | $CH_3$ | H | $R_3 = R_4 = R_5 = H$ |
| S | S | $NH_2$ | $CH_3$ | H | " |
| S | S | $NH_2$ | $CH_3$ | H | $R_3 = CH_3, R_4 = R_5 = H$ |
| S | S | $NH_2$ | $CH_3$ | H | $R_3 = CH_3, R_4 = CH_2CH_2OH, R_5 = H$ |
| O | S | $NH_2$ | $CH_3$ | H | " |
| S | O=S | $NH_2$ | $CH_3$ | H | " |
| S | $CH_2$ | $NH_2$ | $CH_3$ | H | $R_3 = R_4 = R_5 = H$ |
| S | O | $NH_2$ | $CH_3$ | H | " |
| S | O | $NH_2$ | $CH_3$ | $OCH_3$ | " |
| O | O | $NH_2$ | $CH_3$ | $OCH_3$ | $R_3 = CH_3, R_4 = R_5 = H$ |
| S | S | H | $CH_2CH_3$ | H | " |
| S | S | $NH_2$ | $CH_2COOH$ | H | $R_3 = R_4 = R_5 = H$ |
| O | S | $NH_2$ | $CH_2COOH$ | $OCH_3$ | " |
| O | $CH_2$ | OH | $(CH_2)_3COOH$ | H | " |
| O | O | H | $CH_3$ | $SCH_3$ | $R_3 = CH_3, R_4 = R_5 = H$ |
| S | S | $NH_2$ | $C(CH_3)_2COOH$ | H | $R_3 = CH_3, R_4 = OH, R_5 = H$ |
| S | $CH_2$ | $NH_2$ | $CH_3$ | H | $R_3 = CH_3, R_4 = CH_2CH_2OH, R_5 = H$ |
| S | S | $NH_2$ | $C(CH_3)_2COOH$ | H | $R_3 + R_4 = (CH_2)_4, R_5 = H$ |
| S | S | $NH_2$ | $CH_3$ | H | $R_3 = CH_3, R_4 = CH_2CH_3, R_5 = H$ |
| S | O | $NH_2$ | $CH_2COOCH_3$ | NHCHO | $R_3 = R_4 = H, R_5 = CH_3$ |
| S | S | $NH_2$ | $CH_2CONH_2$ | H | $R_3 = CH_3, R_4 = OCH_3, R_5 = H$ |
| S | S | $NH_2$ | $C(CH_3)_2COOH$ | H | $R_3 = CH_3, R_4 = (CH_2)_2OH, R_5 = H$ |
| S | S | H | $CH(CH_3)_2$ | H | " |
| S | $CH(CH_3)_2$ | $NH_2$ | $CH_3$ | H | " |
| S | S | OH | $-(CH_2)_2CONHCH_3$ | H | " |

TABLE 1-continued

| X | Z | R | R₁ | R₂ | Thiazole |
|---|---|----|----|----|----------|
| O | O | OH | —CH₂CON(CH₃)₂ | H | R₃ = CH₃, R₄ = H, R₅ = OCH₃ |

A preferred group of compounds are represented by the formula 1 wherein Z is

or O, especially wherein Z is S. Another preferred group are represented when Z=S and $R_2$ is H or $C_1$–$C_4$ alkoxy, especially methoxy. A further preferred group of compounds is represented by the following formula,

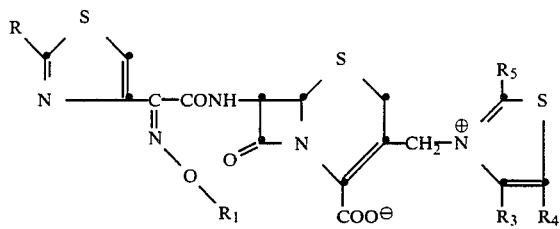

wherein R, $R_1$, $R_3$, $R_4$, and $R_5$ have the same meanings as defined for formula 1. Especially preferred compounds are represented by the above formula when R=amino, $R_1$=$C_1$–$C_4$ alkyl or carboxy-substituted $C_1$–$C_4$ alkyl. Compounds of the above formula wherein $R_1$=methyl and $R_1$ is a group of the formula —C(CH₃)₂(CH₂)₀₋₁COOH or CH₂COOH, CH(CH₃)COOH, and CH₂CH₂COOH are preferred as well as the $C_1$–$C_4$ alkyl esters of such carboxy-substituted alkyl groups. When in the above formula $R_3$ and $R_4$ are taken together with the ring to which they are attached to form a $C_5$–$C_7$ carbocyclic ring, preferred compounds are represented by the following formula,

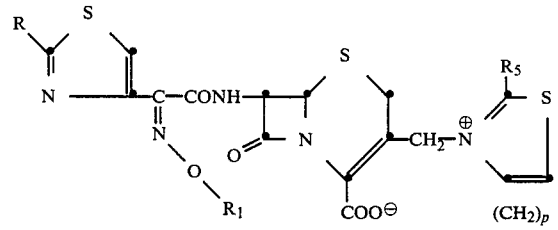

wherein p=3–6.

It will be appreciated that the oximino group, C=N—OR₁, of these compounds can exist in either the syn or anti forms or as a mixture of both forms. The preferred form is the syn form, owing to the general increase in antibacterial activity of the compounds in the syn form over those in the anti form. The compounds are obtained in the syn form by carrying out the abobe-described N-acylations with the syn-oximino-substituted acetic acid.

Examples of preferred compounds are the following:
syn-7β-[2-(2-aminothiazol-4-yl)-2-methoxyiminoacetamido]-3-(thiazolium-3-yl)methyl-3-cephem-4-carboxylate, syn-7β-[2-(2-aminothiazol-4-yl)-2-methoxyiminoacetamido]-3-(4-methylthiazolium-3-yl)methyl-3-cepphem-4-carboxylate,
syn-7β-[2-(2-aminothiazol-4-yl)-2-methoxyiminoacetamido]-3-[4-methyl-5-(2-hydroxyethyl)-thiazolium-3-yl)-3-cephem-4-carboxylate,
syn-7β-[2-(2-aminothiazol-4-yl)-2-methoxyiminoacetamido]-3-(4,5,6,7-tetrahydrobenzthiazolium-3-yl)methyl-3-cephem-4-carboxylate,
syn-7β-[2-(2-aminothiazol-4-yl)-2-(2-carboxyprop-2-yl)oxyiminoacetamido]-3-[4-methyl-2-(2-hydroxyethyl)thiazolium-3-yl)methyl-3-cephem-4-carboxylate, and
syn-7β-[2-(2-aminothiazol-4-yl)-2-(2-carboxyprop-2-yl)oxyiminoacetamido]-3-(4,5,6,7-tetrahydrobenzthiafolium-3-yl)methyl-3-cephem-4-carboxylate.

The compounds represented by the formula 1 wherein R is an amino group form acid addition salts with strong acids such as hydrochloric acid, hydrobromic acid, sulfuric acid and phosphoric acid. Likewise, when $R_1$ is a carboxy-substituted alkyl group, the carboxy group forms salts with physiologically acceptable bases such as the alkali metal and alkaline earth metal hydroxides, carbonates and bicarbonates. An especially useful salt form is the sodium salt of such acids. Such salts are pharmaceutically useful forms of the compounds in the preparation of soluble formulations of the antibiotics.

The compounds of the invention and the pharmaceutically acceptable salts thereof inhibit the growth of bacteria pathogenic to man and animals. They exhibit high potency against the gram-positive and gram-negative microorganisms such as staphylococcus, steptococcus, proteus, pseudomonas, klebsiella, and like organisms. They also exhibit potency against anaerobic microorganisms such as clostridia and enterobacter.

The compounds of the invention (formula 1) are useful in a method for the treatment of infectious diseases which comprises administering to the infected host a compound of the formula 1 in an effective non-toxic dose of between about 5 mg and about 2,000 mg. The therapeutic method of this invention is applicable in human therapy and in veterinary therapy. The dose may be administered in several daily doses as for example twice or three times daily, or it may be a single dose. The particular treatment regime will depend on such factors as the severity of the infection, the particular bacteria involved, the age and general health of the patient, and the tolerance of the individual patient to the antibiotic. The compounds are preferably administered via the intramuscular or intravenous routes.

This invention also provides pharmaceutical formulations comprising a compound represented by the formula 1 and a pharmaceutical carrier. Such formulations contain a compound of the formula 1 in an amount of between about 50 mg and about 2 g. The compounds of the formula 1 may be formulated in the free acid or base form or in the form of a salt. For parenteral use the compound may be made up in dry powder formulations for subsequent dissolution with a suitable diluent. For example, a compound of the formula 1 wherein $R_1$ is a carboxy-substituted alkyl group may be formulated as a dry crystalline powder, an amorphous powder, or as a lyophilized powder, with a suitable physiologically-acceptable base and made up in vials. Upon the addition of a suitable diluent, a solution of the salt of the compound is obtained for injection. Physiologically-acceptable bases include, for example sodium carbonate, potassium carbonate, sodium bicarbonate, or calcium hydroxide. Amines such as diethanolamine, benzylamine, and triethylamine may also be used for this purpose. Amino acids may be used also. Suitable diluents useful for dissolution of the formulations include the commonly used physiological fluids such as Water-for-Injection USP, 5% dextrose, or physiological saline.

The formulations of the invention may also contain additives such as antioxidants, stabilizers, solubilizing agents, and the like. Formulations may be made up for bulk storage in large containers or filled into vials, ampoules or plastic bags for direct administration.

Preferred formulations of this invention comprise a preferred compound as described hereinabove.

A further aspect of this invention comprises the thiazolium substituted 7-amino nucleus compounds represented by the formula 4 and the salts thereof represented by the following formula,

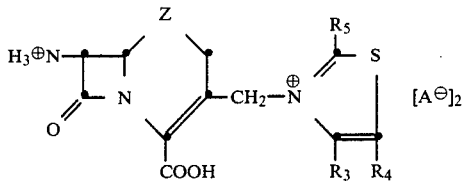

wherein $A^\ominus$ is a halide ion, sulfate ion, nitrate anion or a phosphate anion. Such salts are formed with a strong acid and a nucleus compound 4 by conventional salification procedures.

Examples of such salts are 7-amino-3-(thiazolium)-methyl-3-cephem-4-carboxylic acid dihydrochloride, 7-amino-3-(thiazolium)methyl-3-cephem-4-carboxylic acid dihydrobromide salt, 7-amino-3-(4,5,6,7-tetrahydrobenzthiazolium)methyl-3-cephem-4-carboxylic acid dihydrochloride salt, 7-amino-3-[4-methyl-5-(2-hydroxyethyl)thiazolium]methyl-3-cephem-4-carboxylic acid dihydrochloride salt, and 7-amino-3-(thiazolium)methyl-1-oxa(dethia)-3-cephem-4-carboxylic acid sulfate.

The thiazolium substituted 7-amino nucleus compounds represented by the formula 4 also form mono acid addition salts at the basic 7-amino group. Examples of such salts are the hydrochloride salt, hydrobromide salt, and sulfate salt.

The following Examples are provided to further illustrate and describe the invention.

EXAMPLE 1 syn-7β-[2-(2-Aminothiazol-4-yl)-2-methoxyiminoacetamido]-3-thiazolium-3-ylmethyl-3-cephem-4-carboxylate To a suspension of 910 mg (2 mmole) of syn-7β-[2-(2-aminothiazol-4-yl)-2-methoxyiminoacetamido]-3-acetoxymethyl-3-cephem-4-carboxylic acid in 10 ml of methylene chloride (dried over 4Å sieves) was added at room temperature under nitrogen 1.24 ml (3.5 eq) of mono-trimethylsilyltrifluoroacetamide and the mixture heated to 40° C. in an oil bath. The brown, slightly turbid, solution was cooled to room temperature and 0.426 ml (3 mmole) of TMSI was added. The reaction mixture was stirred for 0.5 hour and evaporated to a thick oil. The oil was dissolved in 10 ml of dry acetonitrile and 0.485 ml (6 mmole) of THF was added and the solution of the silylated 3-iodomethyl derivative was stirred for 10 minutes.

A solution of 0.17 ml (2.4 mmole) of thiazole in 2 ml of dry acetonitrile was added to the above solution of the silylated 3-iodomethyl derivative and the reaction mixture was stirred under nitrogen at room temperature for 2.5 hours. A mixture of 8 ml of acetone and 2 ml of methyl alcohol was added and the precipitate was filtered, washed with acetone and diethyl ether and dried in vacuo at room temperature. There were obtained 596 mg (50% yield) of the product, syn-7β-[2-(2-aminothiazol-4-yl)-2-methoxyiminoacetamido]-3-thiazolium-3-ylmethyl-3-cephem-4-carboxylic acid and iodide salt, contaminated with the unreacted starting material, the corresponding 2-cephem iodide salt, and possibly some 3-cephem lactone, as shown by HPLC.

The iodide salt was converted to the title compound and purified as follows. The crude iodide salt, 590 mg, was dissolved in 6 ml of pH 7 phosphate buffer-acetonitrile by adding sodium bicarbonate. The solution was injected on a reverse phase $C_{18}$ HPLC and the column developed with the solvent system. 5% acetonitrile:2% acetic acid:93% water. The column was run under 100 psi, and at a rate of 6 ml/min, collecting 3 ml fractions. After fraction 84 the solvent was changed to 10% acetonitrile-water. Fractions 49–65 were combined, evaporated to an oil, the oil dissolved in methanol, and the product precipitated upon addition of diethyl ether. The product was sonicated, filtered, washed with diethyl ether and dried to yield 75 mg of title compound.

Mass Spectroscopy: M/e 481 (M+H).

IR (KBr): $cm^{-1}$, 3420, 3413.3, 3405.6, 3395.0, 3391.1, 1770.8 (β-lactam C=O), 1661.8, 1611.6, and 1534.5.

NMRR: 270 MHz (DMSOd$_6$) δ10.5 (s, 1H), 9.53 (d, 1H), 8.93 (d, 1H), 8.3 (d, 1H), 7.21 (s, 2H), 6.72 (s, 1H), 5.66 (dd, 1H), 5.3 (ABq, 2H), 5.06 (d, 1H), 3.81 (s, 3H), and 3.35 (ABq, 2H).

EXAMPLE 2 syn-7β-[2-(2-Aminothiazol-4-yl)-2-methoxyiminioacetamido]-3-(4-methylthiazolium-3-ylmethyl)-3-cephem-4-carboxylate The procedures employed in Example 1 were followed in reacting 910 mg (2 mmole) of syn-7β-[2-(2-aminothiazol-4-yl)-2-methoxyiminoacetamido]-3-acetoxymethyl-3-cephem-4-carboxylic acid in dry methylene chloride with 1.24 ml (3.5 eq) of mono-trimethylsilyltrifluoroacetamide and the trimethylsilyl derivative formed was treated with 0.426 ml (1.5 eq) of TMSI to form the 3-iodomethyl derivative. The latter was allowed to react with 0.22 ml (2.4 mmole) of 4-methylthiazole. After work-up, the product was chromatographed (HPLC) as described in Example 1 to provide 96 mg of the title compound as a white powder.

Mass Spectroscopy: M/e 495 (M+H).

NMR: 270 MHz (DMSOd$_6$) δ10.45 (s, 1H), 9.55 (d, 1H), 7.95 (s, 1H), 7.22 (s, 2H), 6.75 (s, 1H), 5.65 (dd, 1H), 5.26 (s, 2H), 5.10 (d, 1H), 3.82 (s, 3H), 3.32 (ABq, 2H), and 2.56 (s, 3H).

EXAMPLE 3 syn-7β-[2-(2-Aminothiazol-4-yl)-2-methoxyiminoacetamido]-3-[4-methyl-5-(2-hydroxethyl)-thiazolium-3-ylmethyl)-3-cephem-4-carboxylate To a suspension of 27.3 g (60 mmole) of syn-7β-[2-(2-aminothiazol-4-yl)-2-methoxyiminoacetamido]-3-acetoxymethyl-3-cephem-4-carboxylic acid in 200 ml of methylene chloride (dried over 4 Å sieves) was added via syringe at room temperature under nitrogen, 37.3 ml of MSTFA and the mixture was heated to 40° C. in a hot water bath. A brown, slightly turbid, solution formed and was cooled to room temperature and 12.8 ml (90 mmole) of TMSI were added via a syringe. The mixture was stirred at room temperature for 30 minutes and then was evaporated to the 3-iodomethyl derivative obtained as a thick oil. The oil was dissolved in 200 ml of acetonitrile (dried over 3 Å sieves) and 14.6 ml of THF were added and the solution was stirred for 10 minutes at room temperature. A solution of 8.58 ml (72 mmole) of 4-methyl-5-(2-hydroxyethyl)thiazole in acetonitrile treated with 12.8 ml of MSTFA was added dropwise to the solution of the 3-iodomethyl derivative with stirring. The reaction mixture was stirred for 3 hours and then was treated with 85 ml of acetone and 15 ml of methanol. The tan precipitate of the product was filtered, washed with acetone and diethyl ether, and dried at room temperature to afford 31 g of the crude title compound.

The crude product was purified by chromatography as follows. The product was dissolved in aqueous sodium bicarbonate (pH 5.05) and placed on a column packed with 1.8 l of HP-20 resin washed with water. The column was then washed with water. The column was then washed with a continuous gradient of water to 15% aqueous acetonitrile and 125 ml fractions were collected at a slow flow rate. After fraction 34 the column was eluted with 15% aqueous acetonitrile. Fractions 36-45 were combined, treated with acidic alumina to decolorize, and evaporated to an oil. The oil was dissolved in aqueous methanol and the solution diluted with diethyl ether with rapid stirring to precipitate the product as a white solid. The product was filtered, washed with diethyl ether and dried.

UV ($C_2H_5OH$): $\lambda_{max}$ 434 nm, $\epsilon$229, 236 nm, $\epsilon$19,008

IR (KBr): $cm^{-1}$, 3385, 3376, 3374, 3368, 3365, 1773 (β-lactam C=O), 1666, 1613, 1534, and 1036.

NMR: 270 MHz (DMSOd$_6$) δ10.32 (s, 1H), 9.45 (d, 1H), 7.18 (s, 2H), 6.7 (s, 1H), 5.62 (dd, 1H), 5.3 (s, 2H), 5.04 (d, 1H), 3.81 (s, 3H), 3.62 (m, 2H), 3.44 (m, 3H), 3.02 (m, 2H), and 12.47 (s, 3H).

EXAMPLE 4 syn-7β-[2-(2-Aminothiazol-4-yl)-2-methoxyiminoacetamido]-3-(4,5-cyclopentanothiazolium-3-ylmethyl)-3-cephem-4-carboxylate The title compound was obtained by employing the procedures, conditions, reagents and reactants employed in the foregoing Examples and by substituting 4,5-cyclopentanothiazole for the thiazole or substituted thiazole. The product was purified by HPLC.

Mass Spectroscopy: M/e 521 (M+H).

NMR: 270 MHz (DMSOd$_6$) δ10.26 (s, 1H), 9.54 (d, 1H, 7.22 (2, 2H), 6.72 (s, 1H), 5.65 (dd, 1H), 5.25 (ABq, 2H), 5.03 (d, 1H), 3.82 (s, 3H), 3.43 (m, 4H), 2.98 (m, 2H), and 2.53 (m, 2H).

EXAMPLE 5 syn-7β-[2-(2-Aminothiazol-4-yl)-2-methoxyiminoacetamido]-3-(4,5,6,7-tetrahydrobenzthiazolium-3-ylmethyl)-3-cephem-4-carboxylate The title compound was prepared by employing the procedures, conditions, reagents, and reactants employed in the foregoing Examples by substituting 4,5,6,7-tetrahydrobenzothiazole for the thiazole or substituted thiazole. The product was purified by HPLC.

Mass Spectroscopy: M/e 535 (M+H).

NMR: 270 MHz (DMSOd$_6$) δ10.40 (s, 1H), 9.56 (d, 1H), 7.22 (s, 2H), 6.72 (s, 1H), 5.66 (dd, 1H), 5.23 (s, 2H), 5.05 (d, 1H), 3.82 (s, 3H), 3.21 (ABq, 2H), 2.86 (m, 4H), and 1.8 (m, 4H).

I claim:

1. The compound of the formula

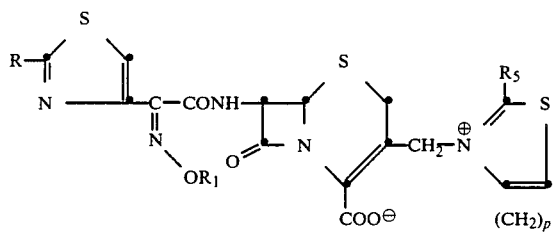

wherein

R is hydrogen, hydroxy, amino, or protected amino;

$R_1$ is hydrogen, $C_1$-$C_4$ alkyl, or $C_1$-$C_4$ alkyl substituted by carboxy, protected carboxy, methoxycarbonyl, ethoxycarbonyl, n-propoxycarbonyl, i-propoxycarbonyl, n-butoxycarbonyl, i-butoxycarbonyl, s-butoxycarbonyl, or a carboxamido group of the formula —CON($R_8$)($R_9$) wherein $R_8$ and $R_9$ are independently hydrogen or $C_1$-$C_3$ alkyl; or $R_1$ is a group of the formula

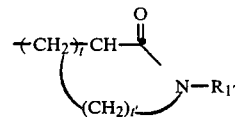

wherein t is 0-3, t' is 2-4, and $R_1'$ is hydrogen or $C_1$-$C_4$ alkyl;

$R_5$ is hydrogen, $C_1$-$C_4$ alkyl, $C_1$-$C_4$ alkoxy, hydroxy, cyano, carboxy, $C_1$-$C_4$ alkoxycarbonyl, amino, $C_1$-$C_4$ alkanoylamino, halogen, $C_1$-$C_4$ alkanoyloxy, $C_1$-$C_4$ alkylsulfonyloxy, or $C_1$-$C_4$ alkyl substituted by hydroxy, $C_1$-$C_4$ alkanoylamino, $C_1$-$C_4$ alkylsulfonyloxy, $C_1$-$C_4$ alkoxy, halogen cyano, carboxy, $C_1$-$C_4$ alkoxycarbonyl, hydroxyimino, or $C_1$-$C_3$ alkoxyimino; and p is an integer of from 3 to 5.

2. The compound of claim 1 wherein R is amino and $R_1$ is $C_1$-$C_4$ alkyl or carboxy-substituted $C_1$-$C_4$ alkyl.

3. The compound of claim 2 of the formula

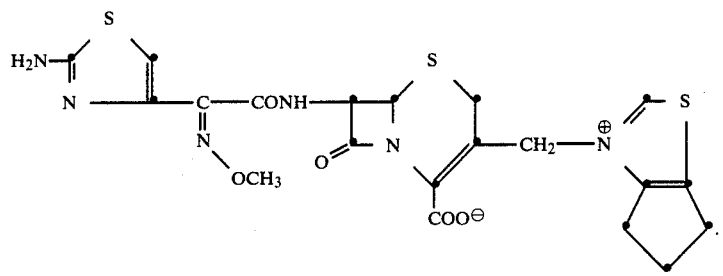

syn

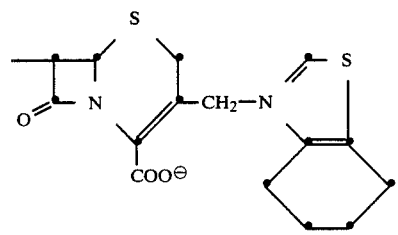

syn

4. The compound of claim 2 of the formula

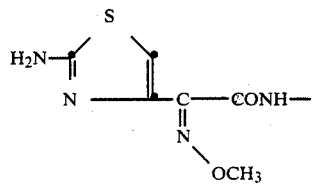

5. A method for treating bacterial infections in mammals which comprises administering to said mammals an antibacterial effective non-toxic dose of a compound of claim 1.

6. The method for treating bacterial infections in mammals which comprises administering to said mammals an antibacterially effective nontoxic dose of a compound of claim 4.

* * * * *

UNITED STATES PATENT AND TRADEMARK OFFICE
CERTIFICATE OF CORRECTION

PATENT NO. : 4,665,066

DATED : May 12, 1987

INVENTOR(S) : John M. Morin, Jr. and Nelson J. Leonard

It is certified that error appears in the above-identified patent and that said Letters Patent is hereby corrected as shown below:

On the title page, left-hand column, under the named inventor "John M. Morin, Jr., Indianapolis, Ind." add the following name as coinventor
-- Nelson J. Leonard, Urbana, Ill. --.

Column 1, in formula 1 under "$R_2$", insert 3 horizontal lines to read

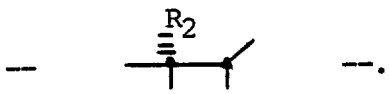

Column 3, line 5, correct "bonylethy" to read -- bonylethyl --.

Column 4, in both structural formulas, under "$R_2$", insert 3 horizontal lines to read

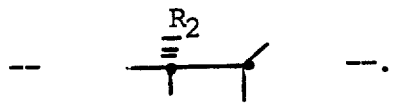

Column 5, in the uppermost formula and the formula at lines 30 to 37, under "$R_2$" insert 3 horizontal lines to read

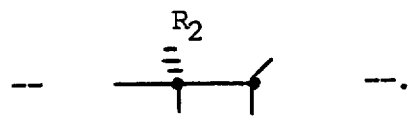

UNITED STATES PATENT AND TRADEMARK OFFICE
CERTIFICATE OF CORRECTION

PATENT NO. : 4,665,066

DATED : May 12, 1987

INVENTOR(S) : John M. Morin, Jr. and Nelson J. Leonard

It is certified that error appears in the above-identified patent and that said Letters Patent is hereby corrected as shown below:

Column 7, line 1, correct "7acylamido-" to read -- 7-acylamido- --; on line 2 correct the spelling of "N-decylation" to read -- N-deacylation --; and on line 31 correct "insert" to read -- inert --.

Column 8, line 35, correct "2-methyl-thiazole" to read
-- 2-methylthiazole --; line 38 correct "5-(2-formuloxyethyl)" to read
-- 5-(2-formyloxyethyl) --; line 46 correct "thiaziole" to read -- thiazole --;
line 56 correct "cyclopheptanothiazole" to read -- cycloheptanothiazole --;
and on line 63 correct "compunds" to read -- compounds --.

Column 9, line 7, correct "2-2-aminothiazol" to read
-- 2-(2-aminothiazol --; line 8 correct "2-thiazol-4-yl)" to read
-- 2-(thiazol-4-yl) --; and on line 9 after "acid", second occurrence,
insert -- 2-(2-hydroxythiazol-4-yl)-2-methoxyiminoacetic acid, --.

Column 11, line 63, correct "abobe-described" to read -- above-described --.

Column 12, line 22, correct "thiafolium" to read -- thiazolium --.

UNITED STATES PATENT AND TRADEMARK OFFICE
CERTIFICATE OF CORRECTION

PATENT NO. : 4,665,066

DATED : May 12, 1987

INVENTOR(S) : John M. Morin, Jr. and Nelson J. Leonard

It is certified that error appears in the above-identified patent and that said Letters Patent is hereby corrected as shown below:

Column 14, line 40, correct "NMRR:" to read -- NMR: --.

Column 15, on the second line of the named title compound under "Example 3", correct "5-(2-hydroxethyl)-" to read -- 5-(2-hydroxyethyl)- --.

Column 16, in the structural formula at lines 25-34, correct that portion of the formula appearing as " 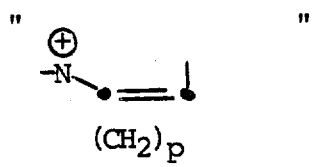 "

to read

-- 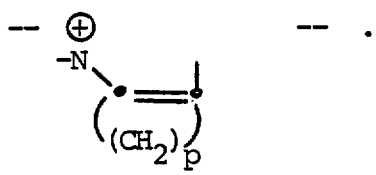 -- .

Signed and Sealed this

Twenty-second Day of March, 1988

Attest:

DONALD J. QUIGG

*Attesting Officer*              *Commissioner of Patents and Trademarks*

Notice of Adverse Decision in Interference

In Interference No. 102,232, involving Patent No. 4,665,066, J. M. Morin, Jr., N. J. Leonard, 3-TETAZOLOMETHYL CEPHALOSPORINS AS ANTIBIOTICS, final judgment adverse to the patentees was rendered Jan. 26, 1990, as to claims 1-6.

*(Official Gazette May 8, 1990)*